(12) United States Patent
Mamiya et al.

(10) Patent No.: US 8,618,501 B2
(45) Date of Patent: Dec. 31, 2013

(54) ION GENERATING DEVICE FOR DUCT

(75) Inventors: Toshio Mamiya, Osaka (JP); Masato Urushisaki, Osaka (JP); Hiroaki Kiyohara, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 233 days.

(21) Appl. No.: 13/320,562

(22) PCT Filed: Feb. 2, 2010

(86) PCT No.: PCT/JP2010/051381
§ 371 (c)(1),
(2), (4) Date: Nov. 15, 2011

(87) PCT Pub. No.: WO2010/137357
PCT Pub. Date: Dec. 2, 2010

(65) Prior Publication Data
US 2012/0056541 A1    Mar. 8, 2012

(30) Foreign Application Priority Data

May 29, 2009  (JP) .................................. 2009-131322
May 29, 2009  (JP) .................................. 2009-131326
May 29, 2009  (JP) .................................. 2009-131329

(51) Int. Cl.
*H01J 27/02* (2006.01)
*H01J 7/44* (2006.01)

(52) U.S. Cl.
USPC ............... 250/423 R; 250/436; 315/111.01; 315/111.81; 315/120; 315/129; 313/12; 313/24; 313/32

(58) Field of Classification Search
USPC ................ 250/423 R, 424, 436; 315/111.01, 315/111.81, 120, 121, 124, 129, 363; 313/12, 24, 25, 32, 35, 39, 325, 359.1, 313/362.1
See application file for complete search history.

(56) References Cited

U.S. PATENT DOCUMENTS

| | | | | |
|---|---|---|---|---|
| 3,256,740 A * | 6/1966 | Tate Kenneth L et al. | ........ | 73/701 |
| 6,958,134 B2 * | 10/2005 | Taylor et al. | ............. | 422/186.04 |
| 7,040,101 B2 * | 5/2006 | Takeda et al. | ....................... | 62/78 |
| 7,312,973 B2 * | 12/2007 | Sekoguchi et al. | ............ | 361/231 |
| 7,863,582 B2 * | 1/2011 | Godyak | ......................... | 250/424 |
| RE43,078 E * | 1/2012 | Cody et al. | .................... | 250/288 |
| 8,492,733 B1 * | 7/2013 | Klochkov et al. | .......... | 250/423 R |
| 2003/0192563 A1 * | 10/2003 | Taylor et al. | .................... | 132/116 |
| 2004/0007000 A1 * | 1/2004 | Takeda et al. | ....................... | 62/78 |
| 2005/0168907 A1 * | 8/2005 | Sekoguchi et al. | ............ | 361/230 |
| 2012/0085921 A1 * | 4/2012 | Nishida | ........................ | 250/424 |
| 2013/0043404 A1 * | 2/2013 | Matsumoto | ................... | 250/424 |
| 2013/0126749 A1 * | 5/2013 | Mamiya et al. | ............ | 250/423 R |

FOREIGN PATENT DOCUMENTS

| | | |
|---|---|---|
| JP | 3-100749 U | 10/1991 |
| JP | 6-78455 A | 3/1994 |
| JP | 7-2619 U | 1/1995 |

(Continued)

*Primary Examiner* — Bernard E Souw
(74) *Attorney, Agent, or Firm* — Birch, Stewart, Kolasch & Birch, LLP

(57) ABSTRACT

Provided is an ion generating device for an air-conditioner duct, which can be easily attached to the inside of an existing air conditioner duct and can ensure a desired ion generation quantity. The ion generating elements of the sub-units (3, 4, 5) of the ion generating device are connected to the drive circuit of the ion generating device main unit (2), and are driven by the drive circuit.

10 Claims, 14 Drawing Sheets

(56) References Cited

FOREIGN PATENT DOCUMENTS

| JP | 3015517 U | 6/1995 |
|----|-----------|--------|
| JP | 2002-277010 A | 9/2002 |
| JP | 2004-353977 A | 12/2004 |
| JP | 2005-33695 A | 2/2005 |
| JP | 2005-337610 A | 12/2005 |
| JP | 2006-167190 A | 6/2006 |
| JP | 2008-241054 A | 10/2008 |
| JP | 2008-301252 A | 12/2008 |
| JP | 2009-103408 A | 5/2009 |

* cited by examiner

ION GENERATING DEVICE FOR DUCT

TECHNICAL FIELD

The present invention is related to an ion generating device that is placed in the vicinity of an outlet port inside a duct such as an air conditioning duct to supply ions to a room.

BACKGROUND ART

The recent demand for energy saving has been tending to increase the number of highly airtight, highly insulated houses, contributing to the increase in demand for air conditioning duct unit for use in such highly airtight, highly insulated houses. Also, hotels and office buildings have conventionally been provided with a central air conditioning system where each room is air-conditioned with air that is conditioned by an air conditioner and supplied through an air conditioning duct extending from the air conditioner to each room. In such an air conditioning system using an air conditioning duct unit or an air conditioning duct, an air-conditioning-duct outlet port is formed in a wall or the ceiling of a room, and conditioned air is introduced into the room through the outlet port.

In one example of such an air conditioning system which has been proposed, there is provided, inside an air conditioning duct, an ion generating device for generating negative ions which are said to have a relaxing effect on human mind and body, such that negative ions generated by the ion generating device are supplied to a room (see Patent Literature 1).

CITATION LIST

Patent Literature

Patent Literature 1: JP-A-2002-277010 (FIG. 24)

SUMMARY OF INVENTION

Technical Problem

In the air conditioning duct unit of Patent Literature 1, an ion generating device, which is integral with a fan unit and thus is allowed to be arranged with only little freedom, is not formed so as to be put and set easily in an already-built-in air conditioning duct via an outlet port. Further, if ions of an amount required according to the size of a room cannot be generated, it may be necessary to provide more ion generating devices; however, it is not easy to provide more AC power supplies, and thus it is difficult to provide more ion generating devices.

In addition, if the ion generating device is disposed outside the outlet port of the air conditioning duct, wiring or the like is exposed to the guest room, and this is ugly to look at and unsightly. This is disadvantageous particularly if the room is a guest room of a hotel, because interior decoration of guest rooms is an important criterion for choosing a hotel.

In a case of disposing ion generating units inside an air conditioning duct of a building after it is built, if a pair of ion generating units are arranged spaced apart from each other in the up-down direction, ions can be effectively discharged. However, in attaching the ion generating units, no screws can be used to fix the ion generating units, because no hole should be formed in the air conditioning duct; further, a double-stick tape is not reliable enough to prevent the ion generating units from falling off or rolling over.

Furthermore, since air conditioning ducts are of various heights, fixed height of the pair of ion generating units will make the ion generating devices hardly versatile. This may be coped with by placing, for example, a length-adjustable pillar between the pair of ion generating units, which are fixed by using a double-stick tape, to make the ion generating devices coincide with the height of the air conditioning duct, to thereby prevent the ion generating devices from falling off or rolling over.

However, if the length of the pillar is adjusted by using a simple sliding mechanism, top and bottom ends of the pillars have to be formed different from each other in shape or size. As a result, an upper pillar-holding portion which is formed in a case of one of the pair of the ion generating devices and a lower pillar-holding portion which is formed in a case of the other ion generating device are different from each other in shape, and thus two different metal molds have to be prepared, which disadvantageously raises the cost.

In the above-described conventional air conditioning duct unit, if the operation status of the ion generating devices is visible from inside the room, the effect of negative ions can also be realized visually, which is preferable. Thus, an operation indicating lamp may be provided in an ion generating device.

However, since ion generating devices are placed inside air conditioning ducts, light from such an operation indicating lamp would be inconveniently difficult to see from inside the room depending on where the outlet port is located and from which direction the operation indicating lamp is seen.

The present invention has been made in view of the foregoing, and an object of the present invention is to provide an ion generating device for ducts which can be easily set inside an already-built-in air conditioning duct and which is capable of securely generating a desired amount of ions. Furthermore, in view of the foregoing, another object of the present invention is to make it possible to adjust the heights of a pair of upper and lower ion generating units which are set inside a duct and simultaneously achieve a significant reduction of cost by using a common metal mold for producing cases of the pair of ion generating units. Moreover, in view of the foregoing, still another object of the present invention is, in a case where an ion generating device which is set inside an air conditioning duct is provided with an operation indicating lamp, to make light from the operation indicating lamp easy to see from inside a room by using a simple method.

Solution to Problem

To achieve the above object, according to one aspect of the present invention, an ion generating device for use in a duct which is used by being set near an outlet port inside the duct includes: a mother ion generating unit including: a flat plate-shaped mother unit case having an opening formed in a flat surface of the flat plate-shaped mother unit case; a mother-unit ion generating element which is attached inside the opening of the mother unit case and has a discharge surface at which positive and negative ions are generated, the discharge surface of the mother-unit ion generating element being exposed through the opening; and a drive circuit which is accommodated in the mother unit case and drives the mother-unit ion generating element; and a daughter ion generating unit including: a flat plate-shaped daughter unit case having an opening formed in a flat surface of the flat plate-shaped daughter unit case; and a daughter-unit ion generating element which is attached inside the opening of the daughter unit case and has a discharge surface at which positive and negative ions are generated, the discharge surface of the daughter-unit ion generating element being exposed through the opening, the daughter ion generating unit being connected to the drive circuit of the mother ion generating unit such that the daughter-unit ion generating element is driven by the drive circuit.

With this configuration, since the ion generating device is composed of separate mother and daughter ion generating units which are connected to each other, the ion generating device can be arranged more freely.

According to the present invention, in the ion generating device for use in a duct configured as described above, it is preferable that the mother ion generating unit include an output terminal having a connector insertion port, and that the daughter ion generating unit include an input terminal having a connector insertion port.

With this configuration, it is possible to connect the daughter ion generating unit to the mother ion generating unit with a connector more easily.

According to the present invention, in the ion generating device for use in a duct configured as described above, it is preferable that the daughter ion generating unit further include an output terminal having a connector insertion port.

With this configuration, it is possible to connect the daughter ion generating unit to another daughter ion generating unit with a connector more easily, which makes it easy to have more daughter ion generating units connected.

Further, to achieve the above object, according to another aspect of the present invention, an ion generating device for use in a duct which is used by being set near an outlet port inside the duct includes: an ion generating unit pair composed of a lower ion generating unit and an upper ion generating unit which are arranged spaced apart from, and facing, each other in an up-down direction; a sliding pillar which couples the lower ion generating unit and the upper ion generating unit of the ion generating unit pair and has an up-down sliding mechanism; and pillar holding portions which are formed in cases of the ion generating unit pair to hold the sliding pillar. Here, the pillar holding portions are shaped to be capable of holding whichever of upper and lower end portions of the sliding pillar.

With this configuration, in which the pillar holding portions provided in both of the cases of the pair of upper and lower ion generating units for holding the sliding pillar are shaped to be capable of holding whichever of the upper and lower end portions of the sliding pillar, it is possible to make the cases of the ion generating unit pair completely equivalent in shape.

Furthermore, according to the present invention, the sliding pillar may have a streamline shape. This helps minimize the reduction of wind quantity, to prevent hindrance to air-conditioning capacity for which the air conditioning duct is originally provided.

Moreover, to achieve the above object, according to another aspect of the present invention, an ion generating device for use in a duct which is used by being set near an outlet port inside the duct includes: a mother ion generating unit including: a flat plate-shaped mother unit case having an opening formed in a flat surface of the flat plate-shaped mother unit case; a mother-unit ion generating element which is attached inside the opening of the mother unit case and has a discharge surface at which positive and negative ions are generated, the discharge surface of the mother-unit ion generating element being exposed through the opening; a drive circuit which is accommodate in the mother unit case and drives the ion generating element; and an operation indicating lamp which indicates a status of operation; and a daughter ion generating unit including: a flat plate-shaped daughter unit case having an opening formed in a flat surface of the flat plate-shaped daughter unit case; and a daughter-unit ion generating element which is attached inside the opening of the daughter unit case and has a discharge surface at which positive and negative ions are generated, the discharge surface of the daughter-unit ion generating element being exposed through the opening, the daughter ion generating unit being connected to the drive circuit of the mother ion generating unit such that the daughter-unit ion generating element is driven by the drive circuit. Here, the mother ion generating unit and the daughter ion generating unit are arranged spaced apart from, and facing, each other in an up-down direction; and a reflector plate is attached to the daughter unit case at a position of the daughter unit case opposite a position where the operation indicating lamp is attached in the mother ion generating unit.

With this configuration, the reflector plate, which is attached to the case of the daughter ion generating unit located at a height different from a height at which the location of the mother ion generating unit is located, reflects light from the operation indicating lamp of the mother ion generating unit. This makes it easier for the light from the operation indicating lamp to be seen from inside the room. For example, even in a case where the outlet port of the duct is located at a position higher than a person's height, and the mother unit is set at the lower portion inside the air conditioning duct, the person can easily recognize the operation status of the ion generating device for an air conditioning duct visually from inside the room.

Furthermore, according to the present invention, the mother unit case may be provided with a light intercepting plate capable of intercepting light from the operation indicating lamp. This makes it possible to intercept the light from the operation indicating lamp with the light intercepting plate if the light from the operation indicating lamp is too disturbing to the eye.

Advantageous Effects of Invention

According to the present invention, since the ion generating device is composed of separate mother and daughter ion generating units which are connected to each other, the ion generating device can be arranged more freely. As a result, it is easy to carry the ion generating device from an outlet port into an existing duct to set the ion generating device inside the duct. Furthermore, it is possible to securely generate a desired amount of ions without increasing the number of AC power supplies. Moreover, even if the ion generating device is set, for example, in a hotel guest room where beautiful interior is indispensable, the ion generating device, which is not visible from inside the guest room, does not spoil the beauty of the guest room.

Furthermore, according to the present invention, since the pillar holding portions formed in both of the cases of the pair of upper and lower ion generating units for holding the sliding pillar are shaped to be capable of holding whichever of the upper and lower end portions of the sliding pillar, it is possible to make the cases of the ion generating unit pair completely equivalent in shape. Furthermore, it is possible to achieve adjustability of the heights of the pair of upper and lower ion generating devices set inside a duct while achieving a significant reduction of cost by using a common mold for producing the cases of the pair of ion generating units.

Moreover, according to the present invention, the reflector plate, which is attached to the daughter unit case, can reflect light from the operation indicating lamp at a height different from the height of the mother ion generating unit. This makes it easier for the light from the operation indicating lamp to be seen from inside a room. For example, even in a case where the outlet port of the duct is located at a position higher than a person's height, and the mother unit is set at the lower portion inside the air conditioning duct, the person can easily recognize the operation status of the ion generating device for use in a duct visually from inside the room.

DESCRIPTION OF EMBODIMENTS

Figure 1:
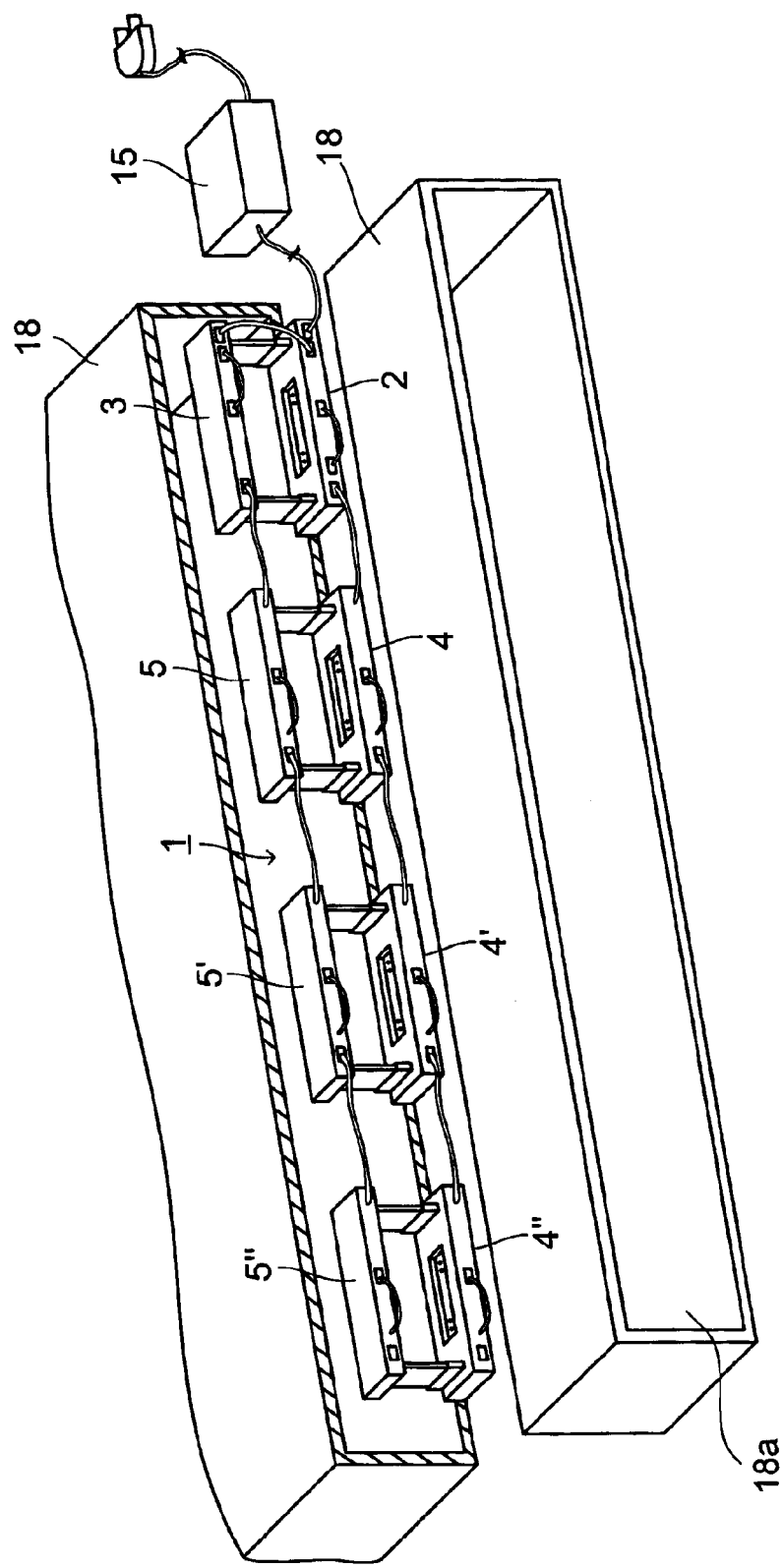
[FIG. 1] A perspective view showing an ion generating device for use in an air conditioning duct embodying the present invention.
Figure 2:
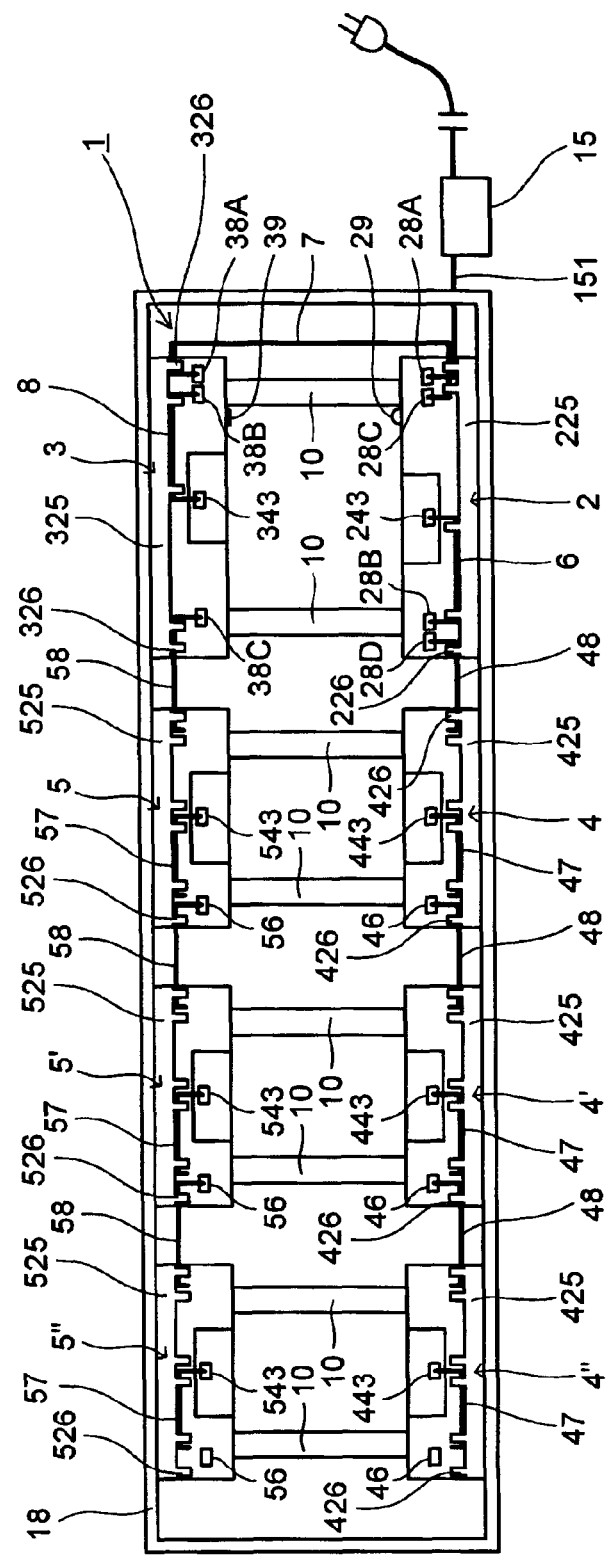
[FIG. 2] A schematic front view showing how the ion generating device is set inside an air conditioning duct.
Figure 3:
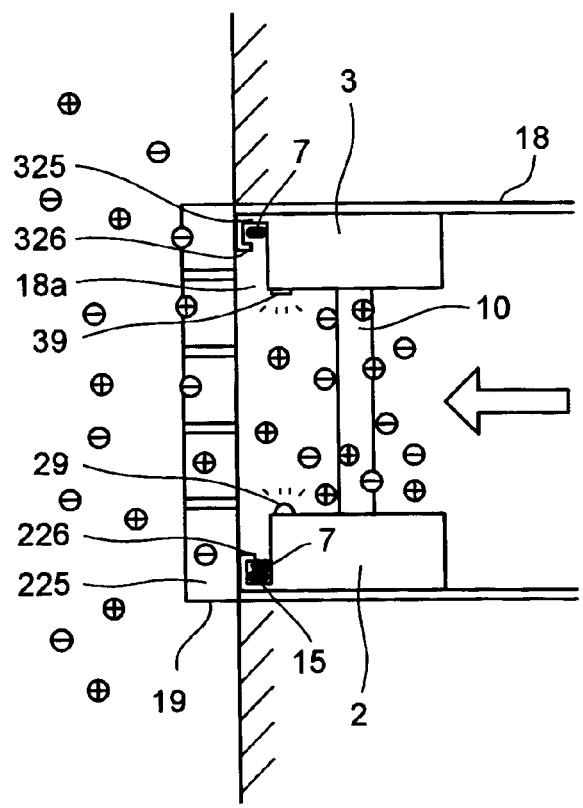
[FIG. 3] A schematic side view showing how the ion generating device is set inside the air conditioning duct.

Hereinafter, embodiments of the present invention will be described with reference to the drawings. The following descriptions will deal with an ion generating device for use in an air conditioning duct as an example of the ion generating device for use in a duct. FIG. 1 is a perspective view showing an ion generating device for use in an air conditioning duct embodying the present invention, FIG. 2 is a schematic front view showing how the ion generating device is set inside an air conditioning duct, and FIG. 3 is a schematic side view showing how the ion generating device is set inside the air conditioning duct. The ion generating device 1 for use in an air conditioning duct is disposed in the vicinity of an outlet port 18a of an air conditioning duct 18 which is already built, for example, in a guest room of a hotel.

As shown in FIGS. 1 to 3, the ion generating device 1 for use in an air conditioning duct is composed of a mother ion generating unit (hereinafter, simply referred to as "mother unit") 2, daughter ion generating units (hereinafter, simply referred to as "daughter units") 3 and 4 which are connected to the mother unit 2, a daughter unit 5 which is connected to the daughter unit 3, a daughter unit 4' which is connected to the daughter unit 4, and a daughter unit 5' which is connected to the daughter unit 5.

In the ion generating device 1 for use in an air conditioning duct, four ion-generating-unit pairs are arranged side by side along a direction which is perpendicular to the air-flow direction of the air conditioning duct 18, each of the four pairs being composed of two ion generating units (the mother unit 2—the daughter unit 3, the daughter unit 4—the daughter unit 5, the daughter unit 4'—the daughter unit 5') which are arranged spaced apart from and facing each other in the up-down direction. The upper and lower ion generating units of each of these pairs are coupled to each other in an up-down direction by sliding pillars 10, 10 which are adjustable in length, so that the height of the position of the upper ion generating unit from the lower ion generating unit can be adjusted.

<Mother Unit 2>

Figure 4:
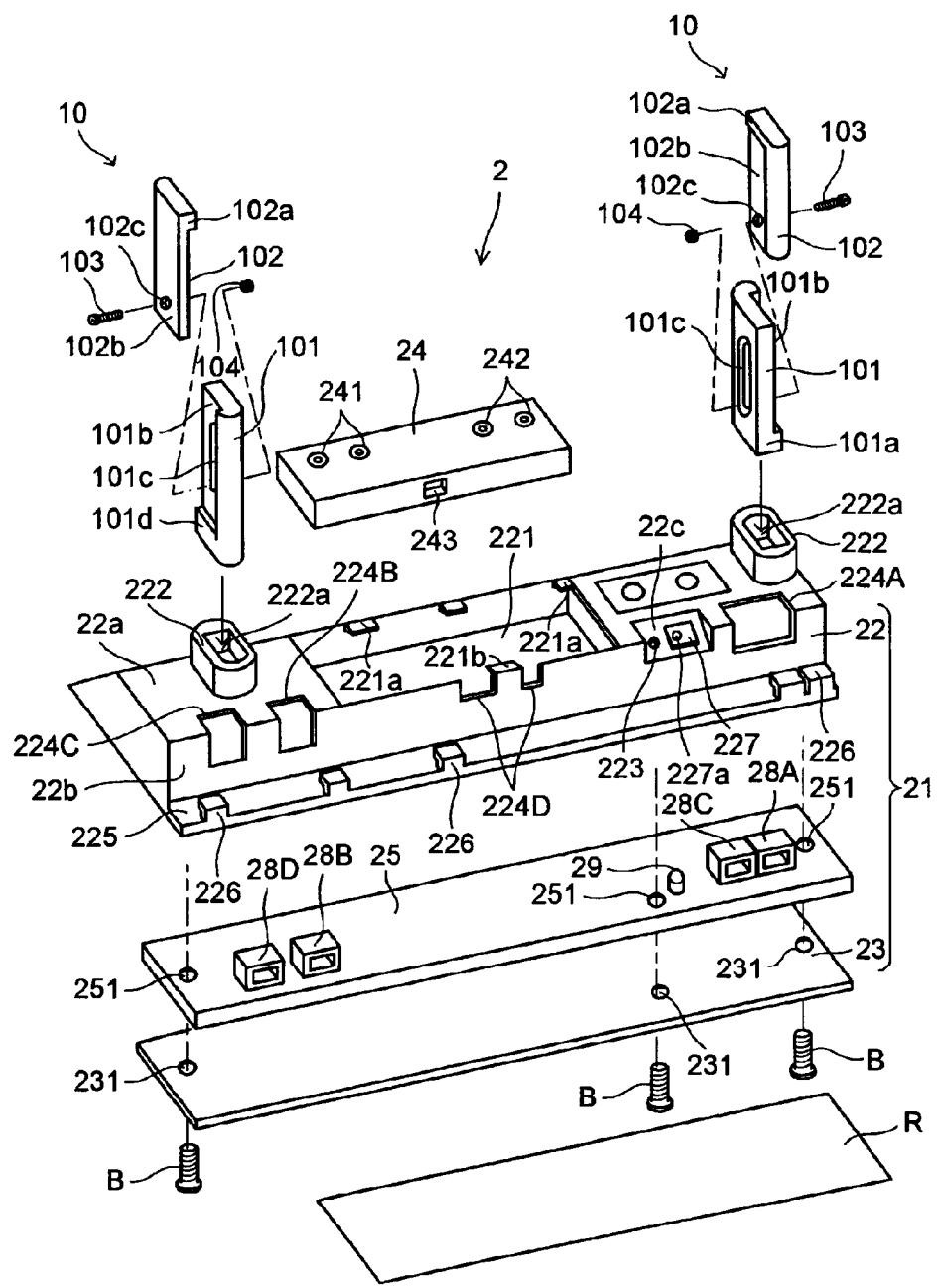
[FIG. 4] An exploded perspective view of a mother ion generating unit.
Figure 5:
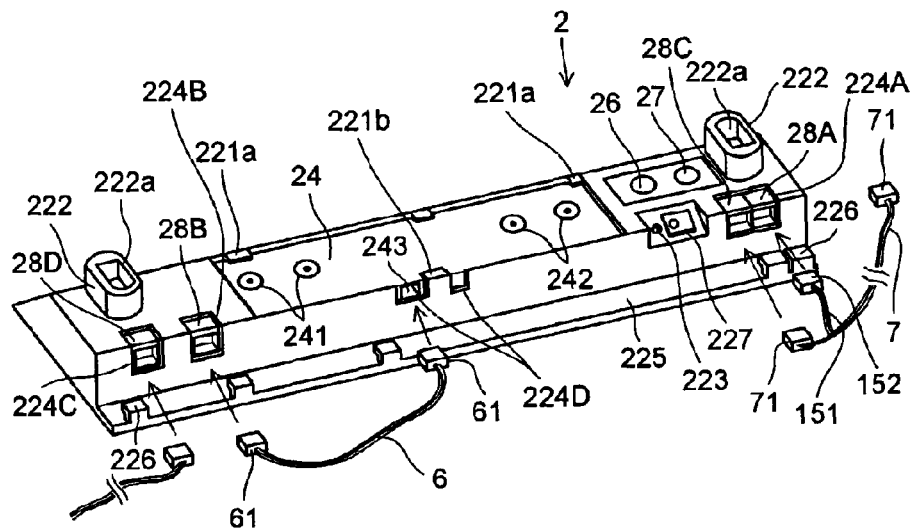
[FIG. 5] A perspective view of the mother ion generating unit.

FIGS. 4 and 5 are an exploded perspective view and a perspective view, respectively, of a mother ion generating unit. The configuration of the mother unit 2 will be described based on FIGS. 4 and 5. The mother unit 2 is configured such that an ion generating element 24 and a circuit board 25 having a drive circuit (not shown) printed on a surface thereof are accommodated in a case 21, the case 21 being a flat-plate shaped outer frame which is made of resin and substantially rectangular in plan. The case 21 is composed of an upper case 22 which has a shape of a bottomless box, and a lower case 23 which has a shape of a plate.

In the lower case 23, screw holes 231 are formed to penetrate the lower case 23, corresponding to a plurality of bosses (not shown) which are formed at proper positions in the upper case 22. The lower case 23 is fixed by being fitted into the upper case 22 to be in contact with inside of the bottom rim of the upper case 22, and thus the bottom case 23 is visible only when the mother unit 1 is seen from below. A double-stick tape R adheres to a bottom surface of the lower case 23 such that one surface of the double-stick tape R is in contact with the bottom surface of the lower case 23.

A rectangular pocket 221 is formed at an upper surface side of the upper case 22. The ion generating element 24, which has a shape corresponding to the cavity of the pocket 221, is fitted in the pocket 221. Along the rear edge of the opening of the pocket 221, there are formed three hooks 221a which engage with the upper surface of the ion generating element 24. A pair of pillar holders 222, 222 are formed on the upper surface of the upper case 22 at both ends thereof in the length direction to protrude therefrom with the pocket 221 placed therebetween. In each of the pillar holders 222, 222, there is formed a bullet-shaped groove 222a into which a corresponding one of the sliding pillars 10, 10 is fitted.

On the upper surface 22a of the upper case 22, a reset button 26 and an operation button 27 are formed. The reset button 26 and the operation button 27 are used to operate a tact switch (not shown) which is correspondingly located on a circuit board 25. An (erroneous) operation of the ion generating element 25 can be reset to the initial state by means of pressing and holding (for example, for three seconds or longer) the reset button 26, and the ion generating element 25 can be made to start or stop operating by means of pressing operation performed on the operation button 27.

In a front surface 22b (the surface facing frontward in FIGS. 4 and 5) of the upper case 22, there are formed terminal windows 224A to 224D through each of which a terminal for connecting a connector is exposed. In particular, the terminal window 224D is located substantially at the center of the front edge of the opening of the pocket 221, and thus is formed as a window without an upper edge. The terminal window 224D is formed wide, and an elastic hook 221b is formed to extend from part of the lower frame of the terminal window 224D. In attaching the ion generating element 24, by elastically deforming the hook 221b toward the front, the ion generating element 24 can be inserted into the pocket 221. After the ion generating element 24 is inserted, when the hook 221b is elastically restored to its initial position, the hook 221b engages with the upper surface of the ion generating element 24 together with the hooks 221a, and thereby the ion generating element 24 can be securely fixed. The ion generating element 24 can be detached from the pocket 221 in the same manner of operation. Thus, the ion generating element 24 can be easily replaced with a new one when, for example, an electrode is degraded and its life is over.

In the upper case 22, there is fanned a slope area 22c which is inclined downward in front of the reset button 26 and the operation button 27. On the slope area 22c, an through hole 223 and a light intercepting plate 227 are formed. The light intercepting plate 227 is pivotally supported by a pivot shaft 227a such that it is pivoted by hand as necessary to cover the through hole 223 to intercept light from an LED 29. For example, light from the LED 29 may bother some people, and in such a case, the light intercepting plate 227 can be used to intercept the light from the LED 29.

A tongue 225 for guiding a cable is formed extending along the lower edge of the front surface 22b of the upper case 22, the tongue 225 protruding forward. Hooks 226 are formed at proper positions of a front end edge of the tongue 225. The hooks 226 are provided for fixing a cable guided on the tongue 225 to prevent the cable from being twisted. The provision of the tongue 225 and the hooks 226 helps eliminate the fear of the cable being cut by air flow which flows through the air conditioning duct 18 or the fear of the connector coming off, and thus enhances the safety of the ion generating device 1.

On a surface of the ion generating element 24, a positive ion generating portion 241 and a negative ion generating portion 242 are formed; the positive ion generating portion 241 generates positive ions in the air by discharging electricity into the air when positive voltage is applied thereto, and the negative ion generating portion 242 generates negative ions in the air by discharging electricity into the air when negative voltage is applied thereto.

Positive voltage is applied to the positive ion generating portion 241, and in a plasma region generated by the discharge, water molecules present in the air are electrically decomposed to mainly produce hydrogen ions $H^+$. Water molecules remaining in the air gather around the thus produced hydrogen ions to form stable positive cluster ions $H^+(H_2O)_m$.

Negative voltage is applied to the negative ion generating portion 242, and in the plasma region generated by the discharge, oxygen molecules present in the air are electrically decomposed to mainly produce oxygen ions $O_2^-$. Water molecules remaining in the air gather around the thus produced oxygen ions to form stable negative cluster ions $O_2^-(H_2O)_n$. Here, m and n are each any integer.

Herein, the term "positive ion" refers to a positive cluster ion, and the term "negative ion" refers to a negative cluster ion. Incidentally, the production of positive and negative cluster ions has been confirmed by time-of-flight mass spectrometry.

The positive and negative ions, when simultaneously discharged into the air, gather on surfaces of microorganisms such as bacteria and viruses and surround them. And the positive and negative ions are instantaneously combined to produce and collect, on the surfaces of the microorganisms, hydroxyl radicals [•OH] and hydrogen peroxides [$H_2O_2$] as highly oxidative active species, which decompose protein forming the surfaces of the microorganisms in a chemical reaction to inhibit the activity of the microorganisms. In addition, it has been known that the hydroxyl radicals [•OH] and hydrogen peroxides [$H_2O_2$] produced as described above also function to decompose odor components in the air. Thus, by generating positive and negative ions and ejecting them from the outlet port 18a of the air conditioning duct 18, it is possible to inactivate viruses floating in a room, extinguish bacteria and fungi existing in the room, and deodorize the room.

An input terminal 243 having a connector insertion port is formed in a side surface of the ion generating element 24 in the lengthwise direction. The input terminal 243 is located at the terminal window 224D of the upper case 22 such that the connector insertion port faces outside of the case 21 through the terminal window 224D. Into the output terminal 243, there is fitted one of connectors 61, 61 formed at both ends of a cable 6 for connecting a circuit board 25 (drive circuit) and the ion generating element 24.

On the circuit board 25, four chip-shaped terminals 28A to 28D and an LED (an operation indicating lamp) 29 are mounted. The four terminals are one input terminal 28A and three output terminals 28B, 28C, and 28D. The input terminal 28A and the output terminal 28C are located at the terminal window 224A of the upper case 22. The output terminal 28C is located at the terminal window 224B of the upper case 22. The output terminal 28D is located at the terminal window 224C of the upper case 22. The connector insertion ports of the terminals face outside of the case 21 via the terminal windows 224A to 224C. In the circuit board 25, screw holes 251 are formed therethrough corresponding to the plurality of bosses (not shown) formed at proper positions in the upper case 22. The circuit board 25 is fixed with screws B to lower ends of the bosses (not shown) of the upper case 22 together with the lower case 23.

Into the input terminal 28A, there is fitted a connector 152, which is attached to an end of an output-side cable 151 of an AC/DC adapter 15,. Into the output terminal 28B, there is fitted the other one of the connectors 61, 61 formed at both ends of a cable 6 for connecting the circuit board 25 (drive circuit) and the ion generating element 24. Into the output terminal 28C, there is fitted one of connectors 71, 71 formed at both ends of a cable 7 for connecting the daughter unit 3 which is paired with the mother unit 2. In adding the daughter unit 4, a connector 481 at an end of a cable 48 extending from the daughter unit 4 is fitted into the output terminal 28D.

Now a description will be given of how the mother unit 2 operates. (DC) power inputted to the input terminal 28A is then inputted to the drive circuit (not shown) formed on the circuit board 25 and to the LED 29. Output from the drive circuit (not shown) is inputted to the ion generating element 25 via the cable 6. Thereby, the ion generating element 25 is driven, and positive and negative ions are generated in the air according to the above described principle. Simultaneously, the LED 29 is turned on. Operation of the ion generating element 25 is controlled by the drive circuit (not shown) based on operation performed on the reset button 26 and the operation button 27.

The output from the drive circuit (not shown) of the mother unit 2 is inputted from the output terminals 28C, 28D via a cable to the daughter units 3, 4, and further to the daughter units 4', 5 via the daughter units 3, 4, and still further to a daughter unit 4" and the daughter unit 5'via the daughter units 4', 5, and still further to a daughter unit 5" via the daughter unit 5'.

<Daughter Unit 3 paired with Mother Unit 2>

Figure 6:
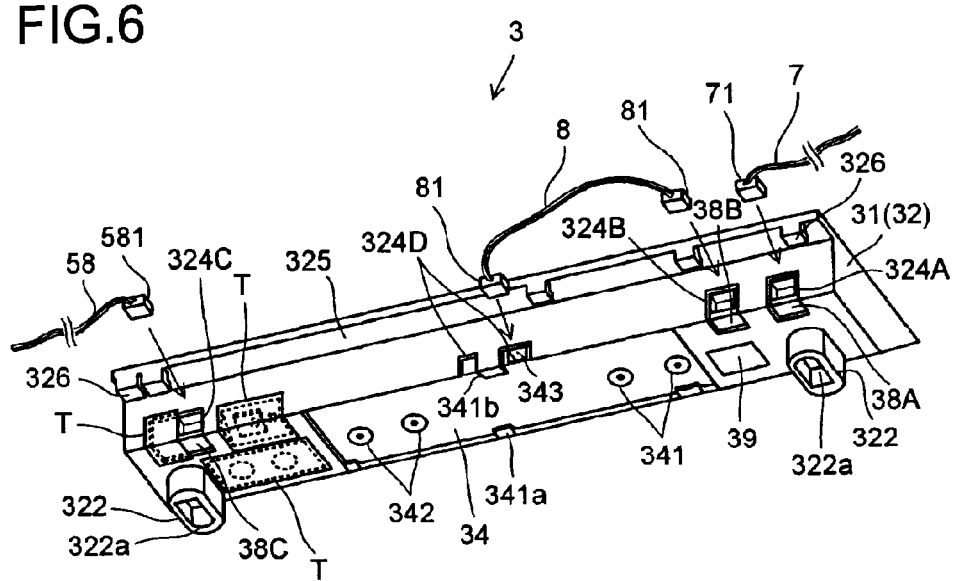
[FIG. 6] An exploded perspective view of a daughter ion generating unit which is paired with the mother ion generating unit.

FIG. 6 is an exploded perspective view of the daughter ion generating unit (daughter unit) 3 which is paired with the mother unit 2. The configuration of the daughter unit 3 will be described based on FIG. 6. The daughter unit 3 is, as shown in FIGS. 1 and 2, an ion generating unit disposed above, and facing, the mother unit 2. Thus, a case 31 of the daughter unit 3 and the mother unit 2 need to be equivalent in length. Here, in view of the metal mold cost, it is preferable to form the cases 21 and 31 of the mother and daughter unit 2 and 3, respectively, as identical resin cases by using the same metal mold. However, the daughter unit 3 does not need the reset button, the operation button, or the through hole, and does not need all of the terminal windows, it is preferable, to distinguish from the mother unit 2, to cover these unnecessary portions by a protection tape T. The daughter unit 3 is disposed above and facing the mother unit 2, in a position that is inverted with respect to the position of the mother unit 2 shown in FIG. 2 in up-down and right-left directions, with its edges all around being aligned with those of the mother unit 2.

The daughter unit 3 is a subordinate ion generating unit that drives an ion generating element 35 based on an input of power from the drive circuit of the mother unit 2. Thus, on a circuit board (not shown) of the daughter unit 3, no drive circuit is formed, and no tact switch or no LED is mounted.

The ion generating element 34 is configured in the same manner as the ion generating element described above. In a side surface of the ion generating element 34 in the length direction, there is formed an input terminal 343 having a connector insertion port. The input terminal 343 is located at a terminal window 324D of the case 31 (a lower case 32), and the connector insertion port faces outside of the case 31 through the terminal window 324D.

A chip-shaped input terminal 38A and chip-shaped output terminals 38B, 38C are mounted on the circuit board (not shown). The input terminal 38A is located at a terminal window 324A of the case 31. The output terminal 38B is located at a terminal window 324B of the case 31. The output terminal 38C is located at the terminal window 324C of the case 31. The connector insertion ports of the terminals respectively face outside of the case 31 via the terminal windows 324A to 324C.

Into the output terminal 343 of the ion generating element 34, there is fitted one of connectors 81, 81 formed at both ends of a cable 8 for connecting the circuit board and the ion generating element 34. Into the input terminal 38A, there is fitted the other one of the connectors 71, 71 formed at both ends of the cable 7 for connecting the mother device 2 and the daughter device 3. Into the output terminal 38B, there is fitted the other one of the connectors 81, 81 formed at both ends of the cable 8 for connecting the circuit board and the ion generating element 34. In adding the daughter unit 5, a connector 581 which is formed at an end of a cable 58 extending from a circuit board of the daughter unit 5 is fitted into the output terminal 38C.

(DC) power inputted to the input terminal 38A is inputted to the ion generating element 34. Thereby, the ion generating element 34 is driven, and positive and negative ions are generated in the air according to the above described principle. Operation of the ion generating element 34 is collectively controlled by the drive circuit (not shown) based on operation performed on the reset button 26 and the operation button 27 of the mother unit 2.

On the case 31 of the daughter unit 3, a reflector plate 39 is bonded to a position opposite, in the up-down direction, to the position where the LED 29 is located in the mother unit 2. The reflector plate 39 reflects light from the LED 29, and this makes it easier to see the light easier from inside the room. Here, if the reflector plate 39 is a mirror, it can clearly reflect the light from the operation indicating lamp. Furthermore, if the reflector plate 39 is made of metal such as stainless steel, it can be produced at low cost. Moreover, if the reflector plate 39 is a convex mirror, it can reflect the light to a wider range of area. Further, if the reflector plate 39 is movable, it can be moved to a position where its reflectivity is optimal, to reflect light from the reflector plate 39 efficiently.

Now, operation of the daughter unit 3 will be described. The power inputted from the drive circuit (not shown) of the mother unit 2 via the cable 7 is then inputted to the ion generating element 35 via the cable 8. Thereby, the ion generating element 35 is driven, and positive and negative ions are generated in the air according to the above described principle. Operation of the ion generating element 35 is collectively controlled on the mother unit 2 side by the drive circuit (not shown) based on operation performed on the reset button 26 and the operation button 27 of the mother unit 2.

<Additional Daughter Unit 4>

Figure 7:
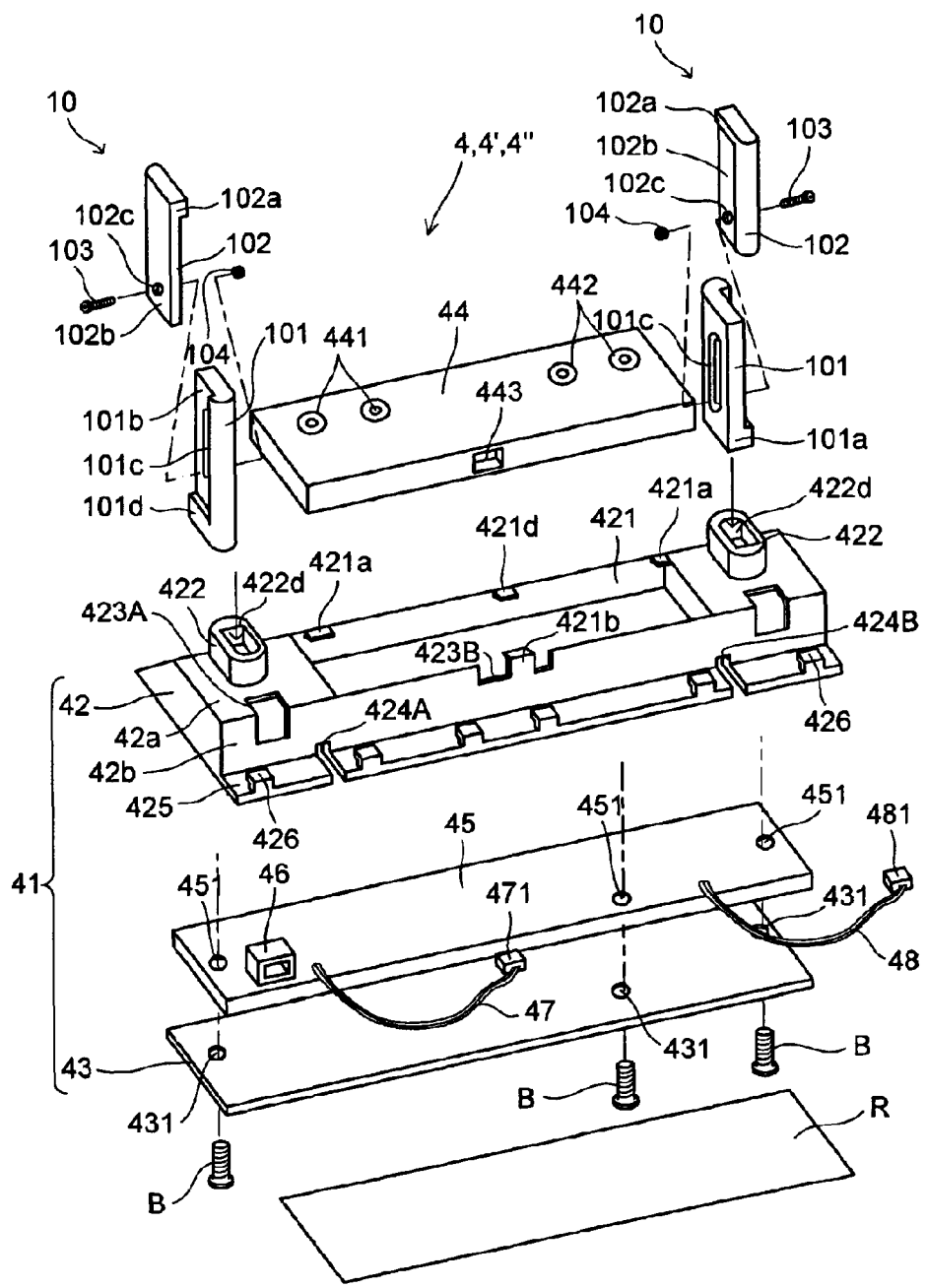
[FIG. 7] An exploded perspective view of an additional daughter ion generating unit.
Figure 8:
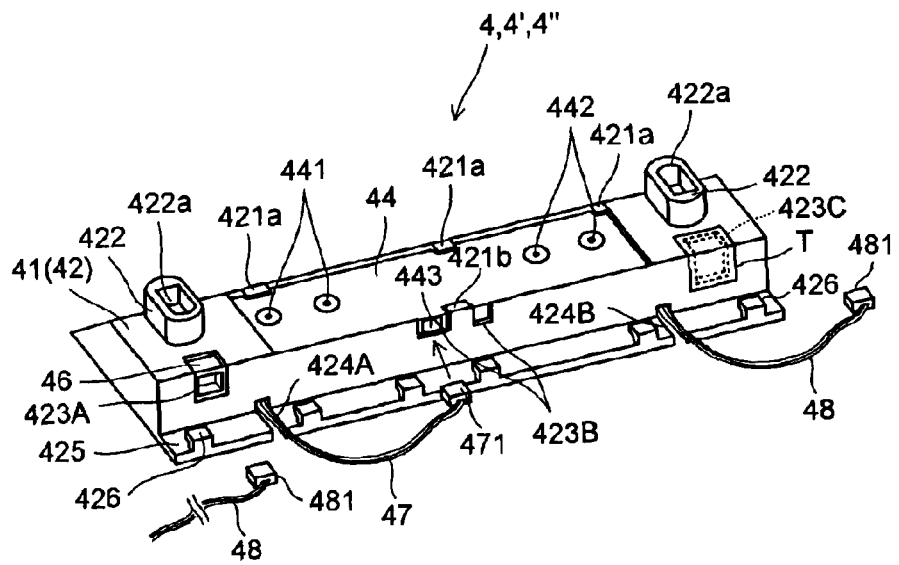
[FIG. 8] A perspective view of the additional daughter ion generating unit.

FIG. 7 and FIG. 8 are an exploded perspective view and a perspective view, respectively, of an additional daughter unit. The configuration of the daughter unit 4 will be described based on FIGS. 7 and 8. As shown in FIG. 1, the daughter unit 4 is a subordinate ion generating unit that is additionally disposed on the mother unit 2 side and that drives an ion generating element 44 based on an input of power from the drive circuit (not shown) of the mother unit 2. Thus, no drive circuit is formed, and no tact switch or no LED is mounted, on a circuit board 45 of the daughter unit 4. The reset switch and the operation switch are also unnecessary, and thus a case 41 of the daughter unit 4 is made smaller in length than the cases of the mother unit 2 and the daughter unit 3. Incidentally, the daughter units 4' and 4" have the same configuration as the daughter unit 4.

In the daughter unit 4, the case 41, which is an outer frame made of resin and substantially rectangular in plan, accommodates the ion generating element 44 and the circuit board 45 on a surface of which a circuit (not shown) is printed. The case 41 is composed of an upper case 42 which has a shape of a bottomless box and a lower case 43 which has a shape of a plate.

In the lower case 43, screw holes 431 are formed to penetrate the lower case 43 corresponding to the plurality of bosses (not shown) which are formed at proper positions in the upper case 22. The lower case 43 is fixed by being fitted into the upper case 42 to be in contact with the inside of the bottom rim of the upper case 42, and thus the bottom case 43 is visible only when the daughter unit 4 is seen from below. A double-stick tape R adheres to a bottom surface of the lower case 43 such that one surface of the double-stick tape R is in contact with the bottom surface of the lower case 43.

A rectangular pocket 421 is formed at an upper surface side of the upper case 42. The ion generating element 44, which has a shape corresponding to the cavity of the pocket 421, is fitted in the pocket 421. Along the rear edge of the opening of the pocket 421, there are formed three hooks 421a which engage with the upper surface of the ion generating element 44. A pair of pillar holders 422, 422 are formed on the upper surface of the upper case 42 at both ends thereof in the length direction to protrude therefrom with the pocket 421 placed therebetween. In each of the pillar holders 422, 422, there is formed a bullet-shaped groove 432a in which a corresponding one of the sliding pillars 10, 10 is fitted.

In a front surface 42b (the surface facing frontward in FIG. 7) of the upper case 42, there are formed terminal windows 423A, 423B, and 423C through each of which a connector insertion port of a terminal is exposed, and openings of through holes 424A, 424B for inserting cables therethrough. The terminal window 423B is located substantially at the center of the front edge of the opening of the pocket 221, and thus is formed as a window without an upper edge. The terminal window 423B is formed wide, and an elastic hook 421b is formed to extend from part of the lower edge of the terminal window 423B. The terminal window 423C in FIG. 7 is unnecessary (dummy) in the daughter unit 4, and thus, as shown in FIG. 8, it is preferable to cover the terminal window 423 with the protection tape T. When the ion generating element 44 is attached, the hook 421b is elastically deformed toward the front to thereby allow the ion generating element 44 to be inserted into the pocket 421. After the ion generating element 44 is inserted, if the hook 421b is elastically restored to its initial position, the hook 421b engages with the upper surface of the ion generating element 44 together with the hooks 421a, and thereby the ion generating element 44 is securely fixed.

A tongue 425 for guiding a cable is found to extend along the lower edge of the front surface 42b of the upper case 42 and to protrude forward from the lower edge of the front surface 42b. Hooks 426 are formed at proper positions of a front end portion of the tongue 425. The hooks 426 are provided for fixing a cable guided on the tongue 425 to prevent the cable from being twisted. The provision of the tongue 225 and the hooks 226 helps eliminate the fear of the cable being cut by air flow which flows through the air conditioning duct 18 or the fear of the connector coming off, and thus enhances the safety of the ion generating device 1.

The ion generating element 44 is configured in the same manner as the ion generating elements described above. In a side surface of the ion generating element 44 in the length direction, there is formed an input terminal 443 having a connector insertion port. The input terminal 443 is located at the terminal window 423B of the upper case 42 such that the connector insertion port faces outside of the case 41 through the terminal window 423B.

A chip-shaped output terminal 46 is mounted on, and ends of two cables 47, 48 are soldered to, the circuit board 45. The output terminal 46 is located at the terminal window 423A, and the connector insertion port faces outside of the case 41 through the terminal window 423A. The cables 47, 48 are drawn out of the case 41 through the through holes 424A, 424B of the upper case 42.

A connector 471, which is formed at an end of the cable 47 extending from the circuit board 45, is fitted into the input terminal 443 of the ion generating element 44. A connector 481, which is formed at an end of the cable 48 extending from the circuit board 45, is fitted into the output terminal 28D (see FIG. 5) of the mother unit 2. In adding the daughter unit 4', a connector 481, which is formed at an end of a cable 48 extending from a circuit board of the additional daughter unit 4', is fitted into the output terminal 46 which is on the circuit board 45.

Now, operation of the daughter unit 4 will be described. Power inputted from the drive circuit (not shown) of the mother unit 2 via the cable 48 is fed to the ion generating element 44 via the cable 47. Thereby, the ion generating element 44 is driven, and positive and negative ions are generated in the air according to the above described principle. Operation of the ion generating element 45 is collectively controlled on the mother unit 2 side by the drive circuit (not shown) based on operation performed on the reset button 26 and the operation button 27 of the mother unit 2.

<Additional Daughter Unit 5 Paired with Daughter Unit 4>

Figure 9:
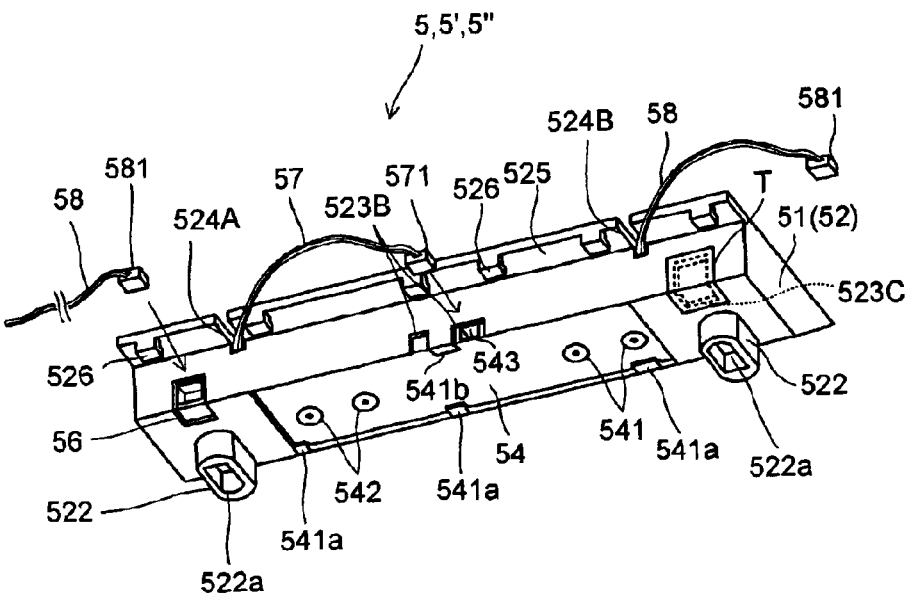
[FIG. 9] A perspective view of a daughter ion generating unit which is paired with the additional daughter ion generating unit.

FIG. 9 is a perspective view of the daughter ion generating unit 5 which is paired with the daughter unit 4. The configuration of the daughter unit 5 will be described based on FIG. 9. As shown in FIG. 1, the daughter unit 5 is added to be placed to a side of the daughter unit 3, which is paired with the mother unit 2, and above the daughter unit 4 such that the daughter unit 4 faces the daughter unit 5. Thus, the length of a case 51 of the daughter unit 5 needs to be equivalent to that of the daughter unit 4. Here, in view of the metal mold cost, it is preferable to form the cases 41, 51 of the daughter units 4, 5, respectively, as identical resin cases by using the same metal mold. The daughter unit 5 is disposed above and facing the daughter unit 4 in a position that is inverted with respect to the position of the daughter unit 4 shown in FIG. 8 in up-down and right-left directions, with its edges all around being aligned with those of the daughter unit 4. Incidentally, the daughter units 5', 5" paired with the daughter units 4' and 4", respectively, have the same configuration as the daughter unit 5.

The daughter unit 5 is a subordinate ion generating unit that drives an ion generating element 54 based on an input of power from the drive circuit (not shown) of the mother unit 2 via the daughter unit 3. Thus, no drive circuit is formed, and no tact switch or no LED is mounted, on a circuit board (not shown) of the daughter unit 5.

The ion generating element 54 is configured in the same manner as the ion generating elements described above. In a side surface of the ion generating element 54 in the length direction, there is formed an input terminal 543 having a connector insertion port. The input terminal 543 is located at a terminal window 523B of the case 51 (a lower case 52), and the connector insertion port faces outside of the case 51 through the terminal window 523B.

A chip-shaped output terminal 56 is mounted on, and ends of two cables 57, 58 are soldered to, a circuit board (not shown). The output terminal 56 is located at a terminal window 523A of the upper case 52 such that a connector insertion port faces outside of the case 51 through the terminal window 523A. The cables 57, 58 are drawn out of the case 51 through slits 524A, 524B of the upper case 52. Half of the terminal window 523C illustrated on the right side in FIG. 9 is unnecessary (dummy) in the daughter unit 5, and thus, as shown in the figure, it is preferable to cover the half of the terminal window 523C with the protection tape T.

A connector 571, which is formed at the end of the cable 57, is fitted into the input terminal 543 of the ion generating element 54. The connector 581 at the end of the cable 58 is fitted into the output terminal 38C of the daughter unit 3. In adding the additional daughter unit 5', the connector 581, which is formed at an end of the cable 58 extending from the circuit board of the daughter unit 5', is fitted into the output terminal 56.

Now, operation of the daughter unit 5 will be described. Power inputted from the drive circuit (not shown) of the mother unit 2 via the daughter unit 3 and through the cable 58 is inputted to the ion generating element 54 via the cable 57. Thereby, the ion generating element 54 is driven, and positive and negative ions are generated in the air according to the above described principle. Operation of the ion generating element 54 is collectively controlled on the mother unit 2 side by the drive circuit (not shown) based on operation performed on the reset button 26 and the operation button 27 of the mother unit 2.

<First Embodiment of Coupling Structure for Coupling Ion Generating-Unit Pair>

Now, a description will be given of a first embodiment of the coupling structure for coupling a pair of ion generating units, using FIGS. 4 to 6. In the pair of mother and daughter ion generating units 2 and 3, and in each of the pairs of the daughter ion generating units 4, 4', 4" and the daughter ion generating units 5, 5', 5", respectively, the two ion generating units are coupled to each other, as upper and lower ion generating units, by a pair of sliding pillars 10, 10 whose lengths are adjustable, such that the distance between the upper ion generating unit and the lower ion generating unit is adjustable. The coupling structure will be described below, with the pair of the mother unit 2 and the daughter unit 3 as an example. Coupling structures used for the pairs of the daughter units 4, 4', 4" and the daughter units 5, 5', 5", respectively, are the same as that used for the pair of the mother unit 2 and the daughter unit 3, and thus overlapping description thereof will be omitted.

If the mother unit 2 and the daughter unit 3 are disposed facing each other in the up-down direction as shown in FIG. 1, the pillar holders 222, 322 formed in the cases 21 and 31 of the mother unit 2 and the daughter unit 3, respectively, face each other in the up-down direction. In this state, the upper and lower end portions of a sliding pillar 10 are fitted into the bullet-shaped grooves 222a, 322a formed in the pillar holders 222, 322, respectively. Thereby, the mother unit 2 and the daughter unit 3 are coupled together.

Each of the sliding pillars 10 is composed of a stationary member 101 that is fitted into one of the pair of right/left pillar holders 222, 222 of the mother unit 2; a sliding member 102 that is fitted into one of the pair of right/left pillar holders 322, 322 of the daughter unit 3; and a bolt 103 and a nut 104 for fixing the stationary member 101 and the sliding member 102 together.

As to the grooves 222a formed in the pair of right/left pillar holders 222, 222 of the mother unit 2, the bullet shapes of the grooves 222a point in opposite directions such that the one in the right pillar holder 222 points backward while the one in the left pillar holder 222 points forward. On the other hand, the grooves 322a formed in the pair of right/left pillar holders 322, 322 of the daughter unit 3 point in opposite directions from those of the mother unit 2, such that the one in the right pillar holder 322 points forward while the one in the left pillar holder 322 points backward.

The grooves of the pillar holders 222 of the mother unit 2 and of the pillar holders 322 of the daughter unit 3 are shaped such that the pillar holders 222 and 322 can hold whichever of the upper portion (an upper end fitting portion 102a) and the lower end portion (a lower end fitting portion 101a) of the sliding pillar 10. This makes it possible to form the cases of the mother unit 2 and the daughter unit 3 such that they are completely equivalent in shape. This makes it possible to use a common metal mold for the cases of the mother unit 2 and the daughter unit 3, which can be expected to have a significant cost reduction effect.

The stationary member 101 and the sliding member 102 of the sliding pillar 10 are resin moldings (pieces) which are in a reflected-image relationship with each other. The description below will deal with the sliding pillar 10 fitted into the right-side pillar holders 222, 322. The sliding pillar 10 fitted into the left-side pillar holders 222, 322 is the same as the one fitted into the right-side pillar holders 222, 322 if it is turned around in the front-rear direction, and thus an overlapping description thereof will be omitted.

Except for the lower end fitting portion 101a which is shaped corresponding to the groove 222a which has a shape of a bullet pointing backward, the stationary member 101 is formed such that a right half portion is cut downward from the upper end and a left half portion is formed as a sickle-shaped portion 101b. A vertically long elongate hole 101c is formed in a side surface of the sickle-shaped portion 101b to penetrate therethrough.

Except for the upper end fitting portion 102a, which is shaped corresponding to the groove 322a which has a shape of a bullet pointing forward, the sliding member 102 is formed such that a left half portion is cut upward from the lower end and a right half portion is fowled as a sickle-shaped portion 102b. A round hole 102c is formed in a lower portion of a side surface of the sickle-shaped portion 102b to penetrate therethrough.

The stationary member 101 and the sliding member 102 are combined together with the sickle-shaped portions 101b and 102b in contact with each other. The shape of the cross section of the sliding pillar 10 resulting from the combining is a streamline (oval) shape, and this helps minimize the reduction in wind quantity to thereby prevent hindrance to air-conditioning capacity for which the air conditioning duct is originally provided.

The bolt 103 is put through the round hole 102c and the elongate hole 101c, and the nut 104 is fitted into an end of the bolt 103. In this way, the stationary member 101 and the sliding member 102 are coupled together. By loosening the engagement of the bolt 103 and the nut 104, the fastened state of the stationary member 101 and the sliding member 102 is released, to allow the sliding member 102 to slide with respect to the stationary member 101 within a range that the bolt 103 is allowed to move in the elongate hole 101c. This makes it possible to change the height position of the daughter unit 3 within that range according to the height size of the air conditioning duct 18.

<Second Embodiment of Coupling Structure for Coupling Ion Generating-Unit Pair>

Figure 10:
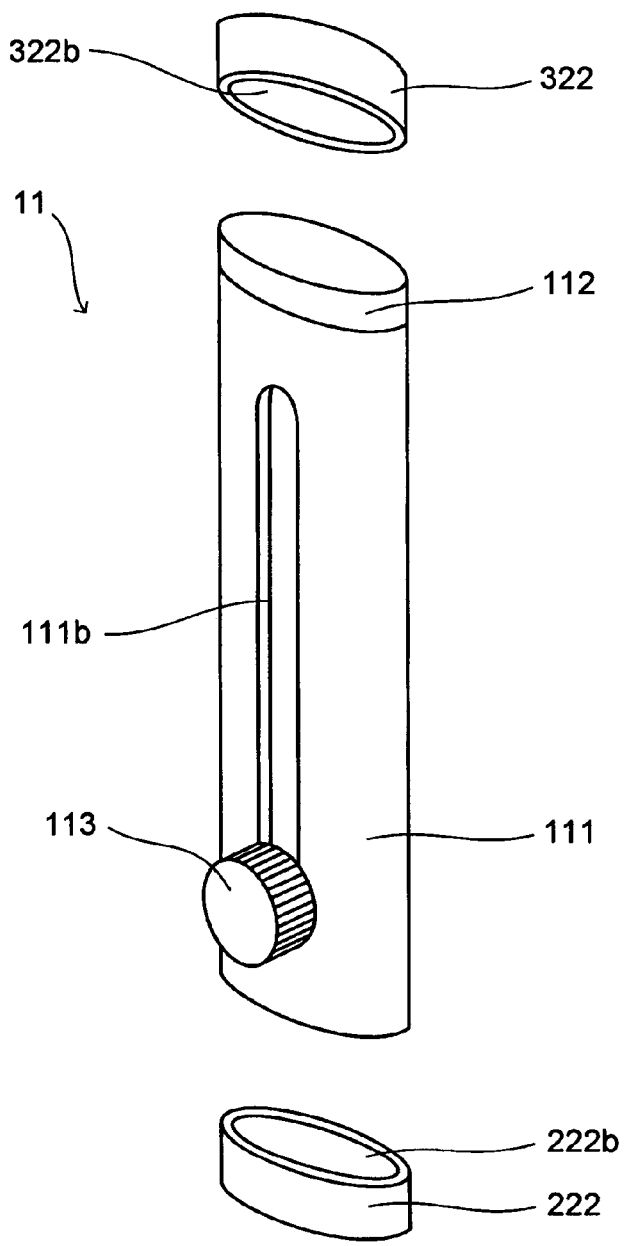
[FIG. 10] A perspective view showing a second embodiment of a coupling structure of a pair of ion generating units.
Figure 11:
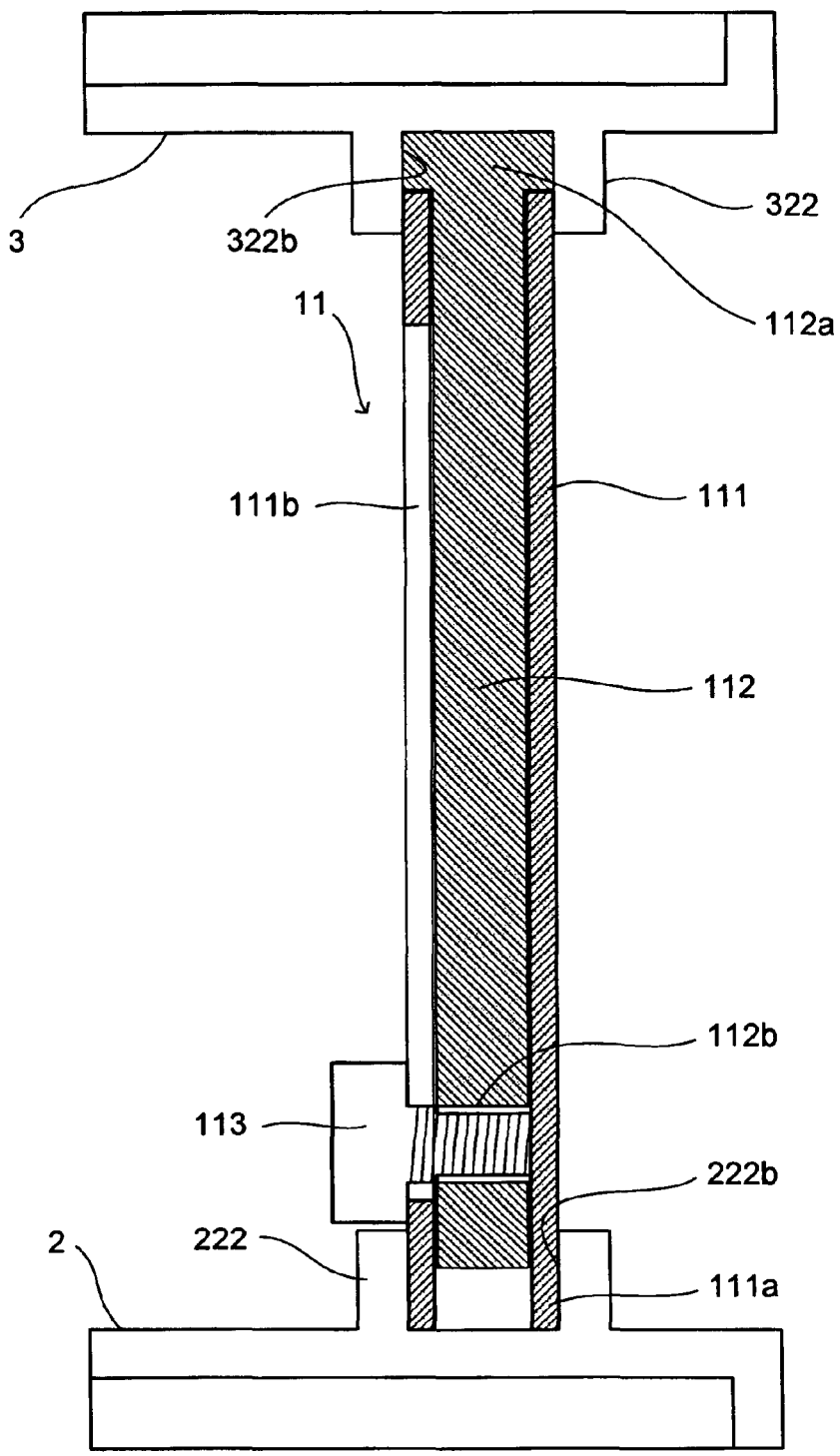
[FIG. 11] A sectional view showing the second embodiment of the coupling structure of a pair of ion generating units.

Now, a description will be given of a second embodiment of the coupling structure for coupling a pair of ion generating units, based on FIGS. 10 and 11. Each of sliding pillars 11 is composed of: a stationary member 111 that is fitted into one of the pair of right/left pillar holders 222, 222 of the mother unit 2; a sliding member 112 that is fitted into one of the pair of right/left pillar holders 322, 322 of the daughter unit 3; and a bolt 113 and a nut 114 for fixing the stationary member 111 and the sliding member 112 together.

Grooves 222b each having an oval circumference, which are respectively formed in the pair of right/left pillar holders 222, 222 of the mother unit 2, are linear oval grooves of an equivalent shape. Grooves 322b each having an oval circumference, which are respectively formed in the pair of right/left pillar holders 322, 322 of the daughter unit 3, are equivalent in shape to the grooves 222b of the mother unit 2.

The grooves of the pillar holders 222 of the mother unit 2 and those of the pillar holders 322 of the daughter unit 3 are shaped such that the pillar holders 222 and 322 can hold whichever of the upper and lower end portions (an upper end fitting portion 112a and a lower end fitting portion 111a) of the sliding pillar 11. This makes it possible to form the cases of the mother unit 2 and the daughter unit 3 in completely the same shape. This makes it possible to use a common metal mold for the cases of the mother unit 2 and the daughter unit 3, which can be expected to have a significant cost reduction effect.

The stationary member 111 and the sliding member 112 of the sliding pillar 11 are resin moldings (pieces) which are in a nested relationship with each other. The description below will deal with the sliding pillar 11 fitted into the right-side pillar holders 222, 322. The sliding pillar 11 fitted into the left-side pillar holders 222, 322 is equivalent to the one fitted into the right-side pillar holders 222, 322 if it is turned around in the front-rear direction, and thus an overlapping description thereof will be omitted.

The stationary member 111 is an oval cylinder that is fitted in contact with the outer periphery of the groove 222b having an oval circumference, and a fitting portion 111a is formed at the lower end portion of the stationary member 111. A vertically long elongate hole 111b is formed through one aspect of the side surface of the stationary member 111 which crosses the short axis of the stationary member 111.

The sliding member 112 is an oval cylinder that is fitted in contact with the outer periphery of the groove 322a having an over circumference, and a fitting portion 112a is formed at the upper end portion of the sliding member 112. A screw hole 112b is formed through a lower portion of one aspect of the side surface of the sliding member 112 which crosses the short axis of the sliding member 112.

The stationary member 111 and the sliding member 112 are combined together with the inner surface of the cavity of the stationary member 111 in contact with the outer surface of the sliding member 112. The shape of the cross section of the sliding pillar 11 resulting from the combining is a streamline (oval) shape, and this helps minimize the reduction of wind quantity to thereby prevent hindrance to air-conditioning capacity for which the air conditioning duct 18 is originally provided.

The screw 113 is inserted through the elongate hole 111b, and is then screwed into the screw hole 112b. In this way, the stationary member 111 and the sliding member 112 are fastened together. By detaching the screw 113 from the screw hole 112b, the fastened state of the stationary member 111 and the sliding member 112 is released, to allow the sliding member 112 to slide with respect to the stationary member 111 within a range that the screw 113 is allowed to move in the elongate hole 111b. This makes it possible to change the height position of the daughter unit 3 within that range according to the height size of the air conditioning duct 18.

<Third Embodiment of Coupling Structure for coupling Ion Generating-Unit Pair>

Figure 12:
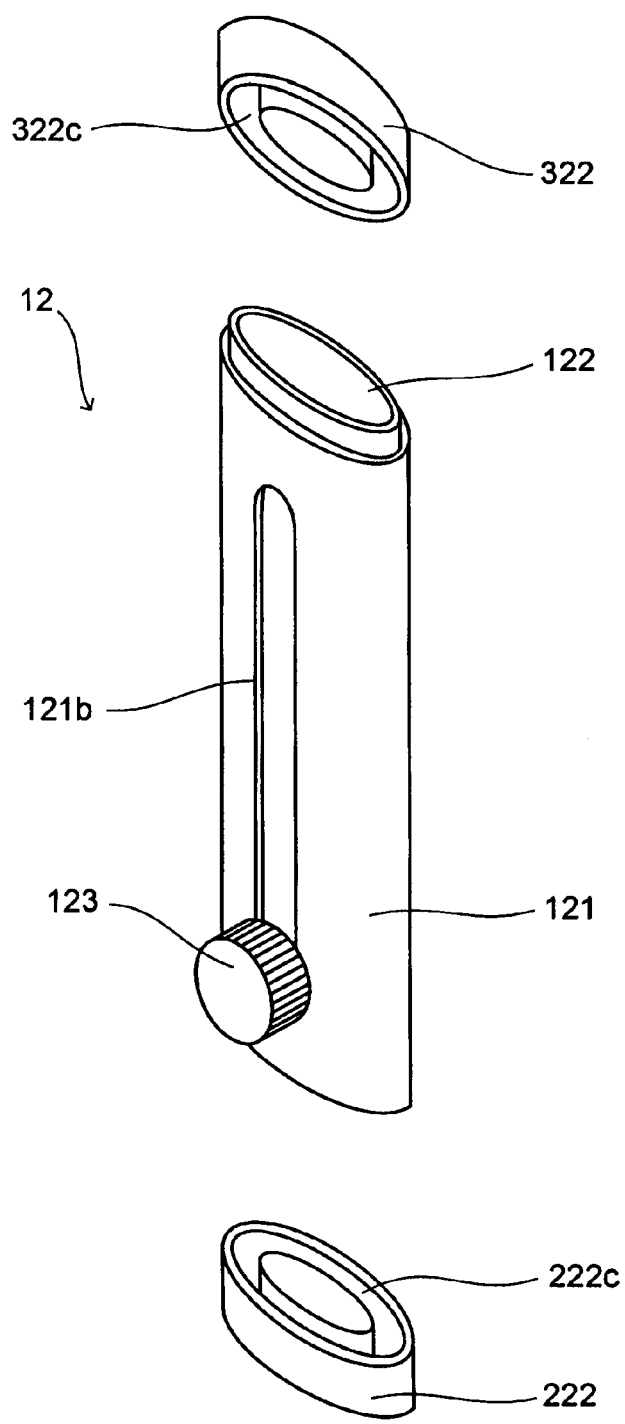
[FIG. 12] A perspective view showing a third embodiment of the coupling structure of a pair of ion generating units.
Figure 13:
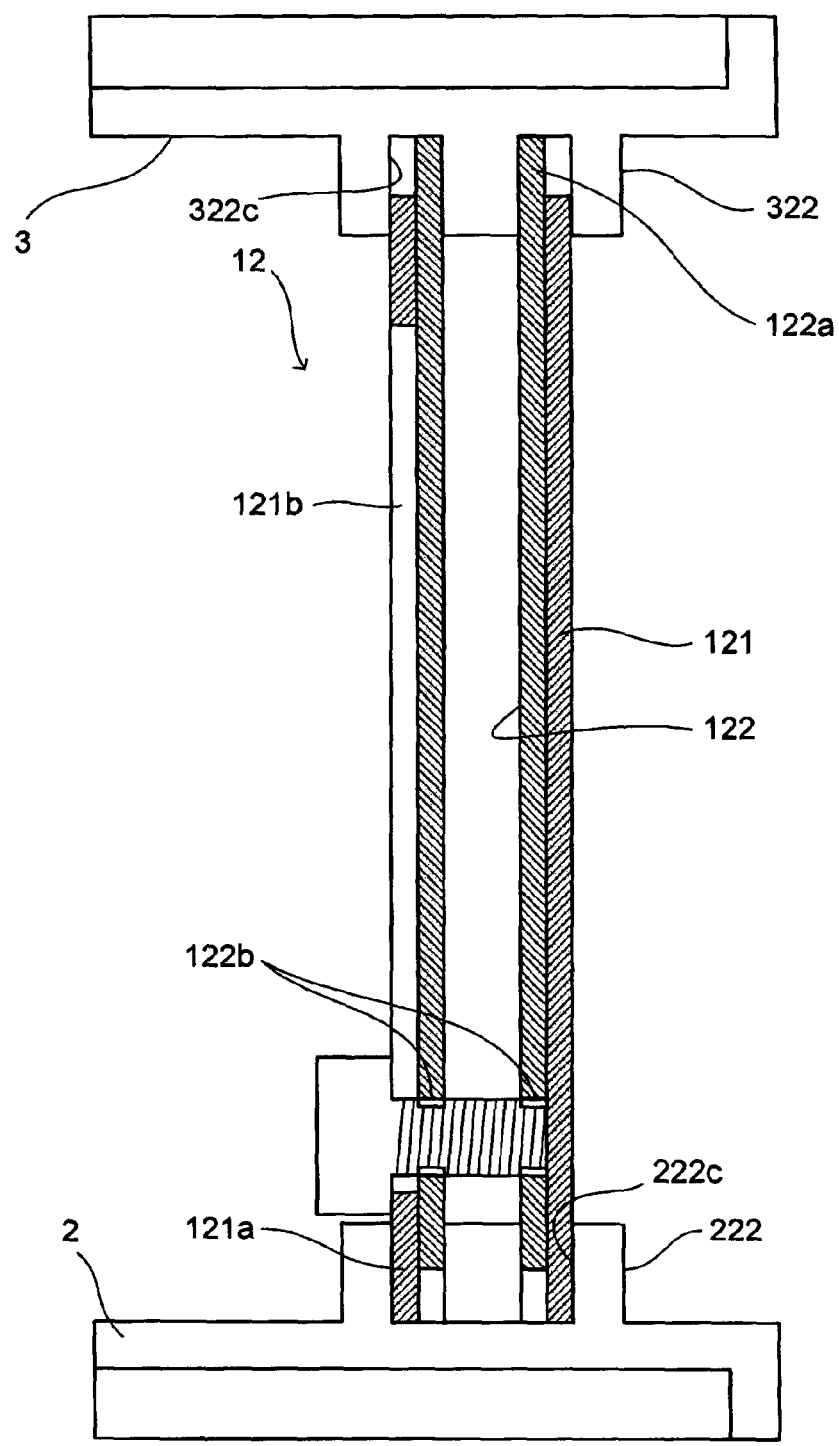
[FIG. 13] A sectional view showing the third embodiment of the coupling structure of a pair of ion generating units.

Now, a description will be given of a third embodiment of the coupling structure for coupling a pair of ion generating units, based on FIGS. 12 and 13. Each of sliding pillars 12 is composed of: a stationary member 121 that is fitted into one of the pair of right/left pillar holders 222, 222 of the mother unit 2; a sliding member 122 that is fitted into one of the pair of right/left pillar holders 322, 322 of the daughter unit 3; and a screw 123 for fixing the stationary member 121 and the sliding member 122 together.

Oval grooves 222c are formed in the pair of right/left pillar holders 222, 222 of the mother unit 2 such that the oval grooves 222c are equivalent to each other in shape. Grooves 322c each having an oval circumference, which are formed in the pair of right/left pillar holders 322, 322 of the daughter unit 3, are equivalent in shape to the grooves 222c of the mother unit 2.

The grooves of the pillar holders 222 of the mother unit 2 and the grooves of the pillar holders 322 of the daughter unit 3 are formed such that the pillar holders 222 and 322 can hold whichever of the upper end portion (an upper end fitting portion 122a) and the lower end portion (a lower end fitting portion 121a) of the sliding pillar 12. This makes it possible to form the cases of the mother unit 2 and the daughter unit 3 in completely the same shape. This makes it possible to use a common metal mold for the cases of the mother unit 2 and the daughter unit 3, which can be expected to have a significant cost reduction effect.

The stationary member 121 and the sliding member 122 of the sliding pillar 12 are resin moldings (pieces) which are in a nested relationship with each other. The description below will deal with, as an example, the sliding pillar 12 fitted into the right-side pillar holders 222, 322. The sliding pillar 12 fitted into the left-side pillar holders 222, 322 is equivalent to the one fitted into the right-side pillar holders 222, 322 if it is turned around in the front-rear direction, and thus an overlapping description thereof will be omitted.

The stationary member 121 is an oval cylinder that is fitted into the groove 222c which is oval in circumference, and a fitting portion 121a is formed at a lower end portion of the stationary member 121. A vertically long elongate hole 121b is formed in one aspect of the side surface of the stationary member 121 which crosses the short axis of the oval section of the stationary member 121.

The sliding member 122 is a dual-diameter oval cylinder which is fitted into the oval groove 322c, and a fitting portion 122a having a large diameter is foamed at an upper end portion of the sliding member 122. A screw hole 122b is formed through a lower portion of one aspect of the side surface of the sliding member 122 which crosses the short axis of the oval section of the sliding member 122.

The stationary member 121 and the sliding member 122 are combined together with the inner surface of the cavity of the stationary member 121 in contact with the outer surface of the sliding member 112. The shape of the cross section of the sliding pillar 12 resulting from the combining is a streamline (oval) shape, and this helps minimize the reduction of wind quantity, to thereby prevent hindrance to air-conditioning capacity for which the air conditioning duct 18 is originally provided.

The screw 114 is inserted through the elongate hole 121b, and is then screwed into the screw hole 122b. In this way, the stationary member 121 and the sliding member 122 are fastened together. By detaching the screw 114 from the screw hole 112b, the fastened state of the stationary member 121 and the sliding member 122 is released, to allow the sliding member 122 to slide with respect to the stationary member 121 within a range that the screw 114 is allowed to move in the elongate hole 121b. This makes it possible to change the height position of the daughter unit 3 within that range according to the height size of the air conditioning duct 18.

<Fourth Embodiment of Coupling Structure for Coupling Ion Generating-Unit Pair>

Figure 14:
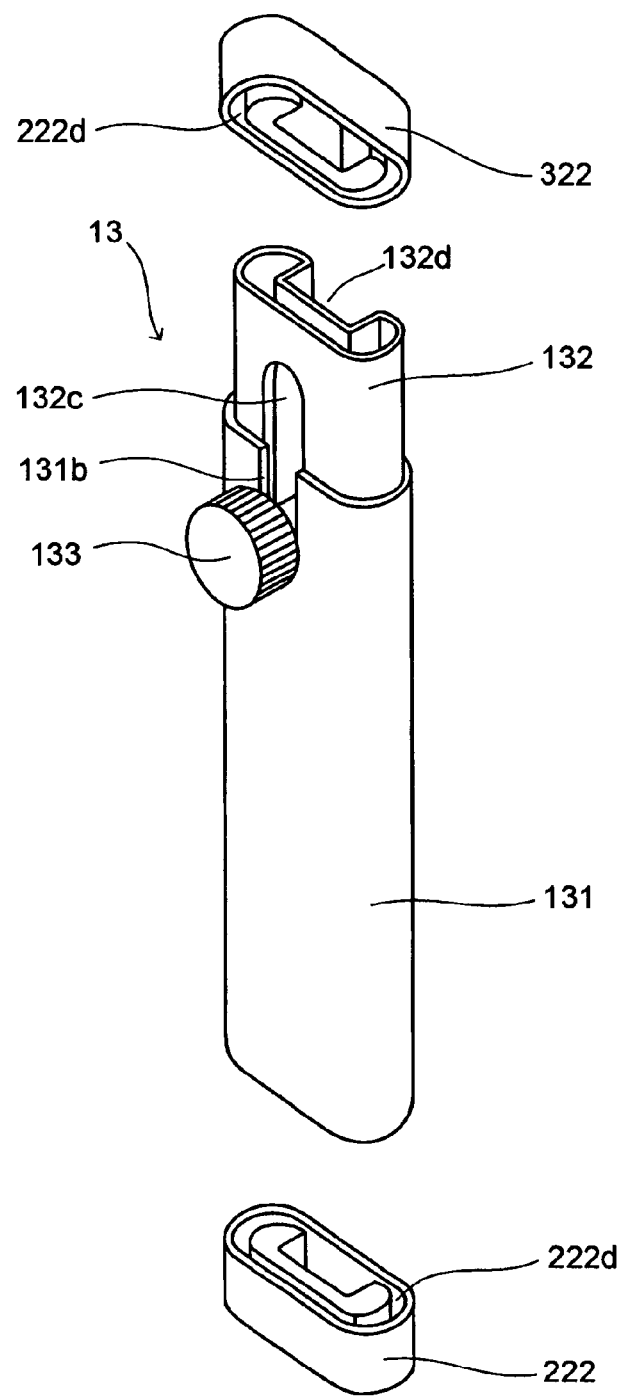
[FIG. 14] A perspective view showing a fourth embodiment of the coupling structure of a pair of ion generating units.
Figure 15:
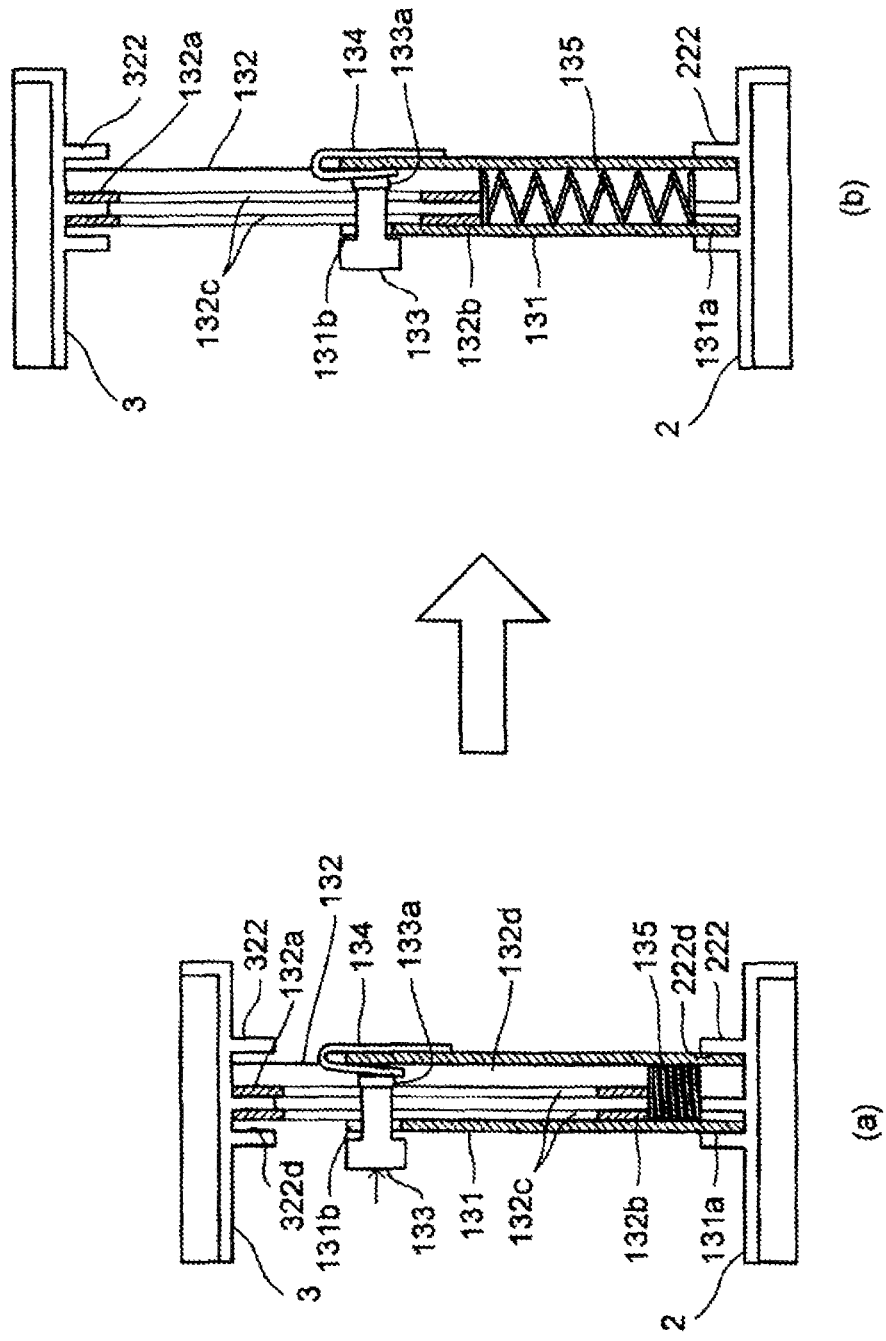
[FIG. 15] A sectional view showing the fourth embodiment of the coupling structure of a pair of ion generating units.
Figure 16:
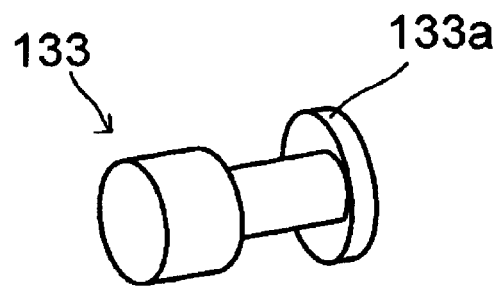
[FIG. 16] A perspective view showing a stopper used in the fourth embodiment of the coupling structure of a pair of ion generating units.

Now, a description will be given of a fourth embodiment of the coupling structure for coupling a pair of ion generating units, based on FIGS. 14 to 16. Each of sliding pillars 13 is composed of: a stationary member 131 that is fitted into one of the pair of right/left pillar holders 222, 222 of the mother unit 2; a sliding member 132 that is fitted into one of the pair of right/left pillar holders 322, 322 of the daughter unit 3; a stopper 133 and a plate spring 134 for fixing the stationary member 131 and the sliding member 132 together; and a compression spring 135 for biasing the sliding member 132 upward.

Grooves 222d are formed in the pair of right/left pillar holders 222, 222 of the mother unit 2. Each of the grooves 222d is formed like an oval moat that surrounds a C-shaped base, and the grooves 222d of the right and left pillar holders 222, 222 are line-symmetric with each other. Grooves 322d formed in the pair of right/left pillar holders 322, 322 of the daughter unit 3 are equivalent in shape to the grooves 222d of the mother unit 2.

The grooves of the pillar holders 222 of the mother unit 2 and of the pillar holders 322 of the daughter unit 3 are shaped such that the pillar holders 222 and 322 can hold whichever of the upper end portion (an upper end fitting portion 132a) and the lower end portion (a lower end fitting portion 131a) of the sliding pillar 10. This makes it possible to form the cases of the mother unit 2 and the daughter unit 3 in completely the same shape. This makes it possible to use a common metal mold for the cases of the mother unit 2 and the daughter unit 3, which can be expected to have a significant cost reduction effect.

The stationary member 131 and the sliding member 132 of the sliding pillar 13 are resin moldings (pieces) which are in a nested relationship with each other. The description below will deal with, as an example, the sliding pillar 13 fitted into the right-side pillar holders 222, 322. The sliding pillar 13 fitted into the left-side pillar holders 222, 322 is equivalent to the one fitted into the right-side pillar holders 222, 322 if it is turned around in the front-rear direction, and thus an overlapping description thereof will be omitted.

The stationary member 131 is an oval cylinder that is fitted in contact with the outer periphery of the groove 222d, and a fitting portion 131a is formed at the lower end portion of the stationary member 131. A vertically long slit 131b is formed in one aspect of the side surface of the stationary member 131 which crosses the short axis of the oval section of the stationary member 131.

The sliding member 132 is a substantially oval cylinder that is fitted in contact with the inner periphery of a groove 322a; a fitting portion 132a that is fitted in contact with the inner periphery of the groove 322a is formed at an upper end portion of the sliding member 132, and at a lower end portion of the sliding member 132, there is formed a press contact portion 132 against which the compression spring 135 is pressed. In an aspect of the side surface of the sliding member 132 which crosses the short axis of the oval section of the sliding member 132, a vertically-elongated rectangular recess 132d is formed, such that the section of the sliding member 132 is substantially C-shaped. A vertically long elongate hole 132c is formed, at a position corresponding to the recess 132d, through each aspect of the side surface of the sliding member 132 which crosses the short axis of the oval section of the stationary member 131.

The stationary member 131 and the sliding member 132 are combined together with the inner surface of the cavity of the stationary member 131 in contact with the outer surface of the sliding member 132. The shape of the cross section of the sliding pillar 13 resulting from the combining is a streamline (oval) shape, and this helps minimize the reduction of wind quantity, to prevent hindrance to air-conditioning capacity for which the air conditioning duct 18 is originally provided.

The stopper 133 is a rivet that has a locking portion 133a at an end thereof. The locking portion 133a is shaped like an oval column whose short diameter is on the order of, and whose longer diameter is larger than, the width of the slit 131b or of the elongate hole 132c. The stopper 133 is inserted through the slit 131b and the elongate hole 132c, and then turned substantially by 90°, so that it does not come off from the elongate hole 132c. In this state, an end surface of the locking portion 133a is pressed against an elastic piece of the plate spring 134, and at the opposite surface, the locking portion 133a is pressed against a wall surface around the elongate hole 132c. In this way, the stopper 133 is locked and the sliding member 132 is fixed to the stationary member 131.

The plate spring 134 is hairpin-shaped, and it is immovably hooked on the upper end portion of the stationary member 131. The elastic piece of the plate spring 134 is located in the recess 132d of the sliding member 132 to bias the sliding member 132 leftward via the stopper 133.

The compression spring 135 is put in the cavity of the stationary member 131 with the stationary member 131 fitted into the pillar holder 222. The compression spring 135 is located between the pillar holder 222 and the sliding member 132, to bias the sliding member 132 upward.

As shown in FIG. 15(a), by pressing the stopper 133 with a finger against the bias force of the plate spring 134, the locking of the stopper 133 is released, to allow the sliding member 132 to slide with respect to the stationary member 131 in a range in which the stopper 133 is allowed to move in the elongate hole 132c. Simultaneously, as shown in FIG. 15(b), the compression spring 135 biases the sliding member 132 upward, and consequently the sliding pillar 13 is elongated. By removing the finger off the stopper 133, the plate spring 134 starts exerting force again to make the sliding member 132 non-slidable. In this way, it is possible to change the height position of the daughter unit 3 within that range according to the height size of the air conditioning duct 18. This embodiment is advantageous in that the height position of the daughter unit 3 can be changed by a single push of the stopper 133.

<Setting of Ion Generating Device inside Air Conditioning Duct>

Before carrying the ion generating device 1 for use in an air conditioning duct inside the air conditioning duct 18, each pair of ion generating units are assembled and wiring between the ion generating units are completed. The lengths of the sliding pillars that couple the pairs of the ion generating units are set the shortest.

Then, a diffuser 19 which is attached to the outlet port 18a of the air conditioning duct 18 is detached, the four pairs of ion generating units, namely, mother unit 2—daughter unit 3, daughter unit 4—daughter unit 5, daughter unit 4'—daughter unit 5', and daughter unit 4"—daughter unit-5", are carried into the air conditioning duct 18, and arranged side by side along a direction perpendicular to the air-flow direction of the air conditioning duct 18. The number of the pairs of the ion generating units is merely an example, and the number may be determined according to the lateral width of the air conditioning duct 18.

At this time, films are removed from lower surfaces of the double-stick tapes R attached to the bottom surfaces of the cases of the lower ion generating units 2, 4, 4', and 4", and the lower ion generating units 2, 4, 4', and 4" are bonded to the inner surface of a lower portion of the wall of the air conditioning duct 18 at constant intervals. The sliding pillars between the upper and lower units are extended corresponding to the height size of the air conditioning duct 18, and thereby the upper ion generating units 3, 5, 5', and 5" are fixed in a state where the top surfaces of the cases of the units are pressed against the inner surface of an upper portion of the wall of the air conditioning duct 18. In attaching the diffuser 19 to the outlet port 18a, positioning is possible by striking the tongues protruding from the cases of the mother and daughter units against the rear end of the diffuser 19.

As hitherto described, the ion generating device 1 for use in an air conditioning duct is composed of the mother unit 2 having a drive circuit and the daughter units 3, 4, 4', 5, and 5' having no drive circuit, which are separate from each other, to improve the degree of freedom in arrangement. As a result, it is easy to carry the ion generating device from the outlet port into the air conditioning duct 18 to set the ion generating device there. Furthermore, it is possible to securely generate a desired amount of ions without increasing the number of AC power supplies. Moreover, even if the ion generating device is set in a hotel guest room where beautiful interior is indispensable, the ion generating device is invisible from inside the guest room, and thus the beauty of the guest room is not spoiled.

When the ion generating device 1 for use in an air conditioning duct which is set as described above is operated, along with generation of ions, light from the LED 29 is reflected by the reflector plate 39 at a height different from the height of the mother unit 2. This makes it easy for a person in a room to see the light from the LED 29. For example, even in a case where the outlet port 18a of the air conditioning duct 18 is located at a position higher than a person's height, and the mother unit is set at the lower portion inside the air conditioning duct 18, the person inside the room can easily recognize the operation status of the ion generating device 1 for use in an air conditioning duct.

It should be understood that the embodiments of the invention described above are not meant to limit the technological idea of the invention in any way.

INDUSTRIAL APPLICABILITY

The present invention is applicable to ion generating devices to be used by being disposed inside a duct such as an air conditioning duct.

LIST OF REFERENCE SYMBOLS 1 ion generating device for use in an air conditioning duct
2 mother ion generating unit
21 mother unit case
3, 4, 4', 4", 5, 5', 5" ion generating daughter unit
31 case of ion generating daughter unit 3
41 case of ion generating daughter unit 4, 4', or 4"
51 case of ion generating daughter unit 5, 5', or 5"
222, 322, 422, 522 pillar holder (pillar holding portion)
225, 325, 425, 525 tongue
226, 326, 426, 526 hook
222a, 322a, 422a, 522a groove (pillar holding portion)
222b, 222c, 222d another embodiment of groove (holding portion)
28A, 38A, 46 input terminal
28B, 28C, 28D, 38B, 38C, 56 output terminal
24, 34, 44, 54 ion generating element
243, 343, 443, 543 input terminal
29 LED (operation indicating lamp)
39 reflector plate
227 intercepting plate
6, 7, 8, 47, 48, 57, 58 cable
61, 71, 81, 471, 481, 571, 581 connector
10 sliding pillar
11, 12, 13 another embodiment of sliding pillar

The invention claimed is:
1. An ion generating device for use in a duct which is used by being set near an outlet port inside the duct, the ion generating device comprising:
a mother ion generating unit including:
a flat plate-shaped mother unit case having an opening formed in a flat surface of the flat plate-shaped mother unit case;
a mother-unit ion generating element which is attached inside the opening of the mother unit case and has a discharge surface at which ions are generated, the discharge surface of the mother-unit ion generating element being exposed through the opening; and
a drive circuit which is accommodated in the mother unit case and drives the mother-unit ion generating element; and
a daughter ion generating unit including:
a flat plate-shaped daughter unit case having an opening formed in a flat surface of the flat plate-shaped daughter unit case; and
a daughter-unit ion generating element which is attached inside the opening of the daughter unit case and has a discharge surface at which ions are generated, the discharge surface of the daughter-unit ion generating element being exposed through the opening, the daughter ion generating unit being connected to the drive circuit of the mother ion generating unit such that the daughter-unit ion generating element is driven by the drive circuit.

2. The ion generating device for use in a duct according to claim 1,
wherein
the mother ion generating unit includes an output terminal having a connector insertion port; and
the daughter ion generating unit includes an input terminal having a connector insertion port.

3. The ion generating device for use in a duct according to claim 2,
wherein
the daughter ion generating unit further includes an output terminal having a connector insertion port.

4. The ion generating device for use in a duct according to claim 1,
wherein
the mother ion generating unit and the daughter ion generating unit are arranged side by side in a direction perpendicular to an air-flow direction of the duct in which air flows.

5. An ion generating device for use in a duct which is used by being set near an outlet port inside the duct, the ion generating device comprising:
an ion generating unit pair composed of a lower ion generating unit and an upper ion generating unit which are arranged spaced apart from, and facing, each other in an up-down direction;
a sliding pillar which couples the lower ion generating unit and the upper ion generating unit of the ion generating unit pair and has an up-down sliding mechanism; and
pillar holding portions which are formed in cases of the ion generating unit pair to hold the sliding pillar,
wherein
the pillar holding portions are shaped to be capable of holding whichever of upper and lower end portions of the sliding pillar.

6. The ion generating device for use in a duct according to claim 5, wherein the sliding pillar has a streamline shape.

7. An ion generating device for use in a duct which is used by being set near an outlet port inside the duct, the ion generating device comprising:
a mother ion generating unit including:
a flat plate-shaped mother unit case having an opening formed in a flat surface of the flat plate-shaped mother unit case;
a mother-unit ion generating element which is attached inside the opening of the mother unit case and has a discharge surface at which ions are generated, the discharge surface of the mother-unit ion generating element being exposed through the opening;

a drive circuit which is accommodate in the mother unit case and drives the ion generating element; and an operation indicating lamp which indicates a status of operation; and a daughter ion generating unit including:

a flat plate-shaped daughter unit case having an opening formed in a flat surface of the flat plate-shaped daughter unit case; and a daughter-unit ion generating element which is attached inside the opening of the daughter unit case and has a discharge surface at which ions are generated, the discharge surface of the daughter-unit ion generating element being exposed through the opening, the daughter ion generating unit being connected to the drive circuit of the mother ion generating unit such that the daughter-unit ion generating element is driven by the drive circuit, wherein the mother ion generating unit and the daughter ion generating unit are arranged spaced apart from, and facing, each other in an up-down direction; and a reflector plate is attached to the daughter unit case at a position of the daughter unit case opposite a position where the operation indicating lamp is attached in the mother ion generating unit.

8. The ion generating device for use in a duct according to claim 7, wherein the mother unit case is provided with a light intercepting plate capable of intercepting light from the operation indicating lamp.

9. The ion generating device for use in a duct according to claim 2, wherein the mother ion generating unit and the daughter ion generating unit are arranged side by side in a direction perpendicular to an air-flow direction of the duct in which air flows.

10. The ion generating device for use in a duct according to claim 3, wherein the mother ion generating unit and the daughter ion generating unit are arranged side by side in a direction perpendicular to an air-flow direction of the duct in which air flows.

* * * * *